US012622681B2

(12) United States Patent
Miyachi et al.

(10) Patent No.: US 12,622,681 B2
(45) Date of Patent: May 12, 2026

(54) ULTRASOUND DIAGNOSTIC APPARATUS, CONTROL METHOD OF ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventors: Yukiya Miyachi, Kanagawa (JP); Tomoki Inoue, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 667 days.

(21) Appl. No.: 17/498,877

(22) Filed: Oct. 12, 2021

(65) Prior Publication Data

US 2022/0022849 A1 Jan. 27, 2022

Related U.S. Application Data

(63) Continuation of application No. PCT/JP2020/016285, filed on Apr. 13, 2020.

(30) Foreign Application Priority Data

Apr. 17, 2019 (JP) ................................. 2019-078241

(51) Int. Cl.
| | |
|---|---|
| *A61B 8/00* | (2006.01) |
| *A61B 8/06* | (2006.01) |
| *A61B 8/08* | (2006.01) |

(52) U.S. Cl.
CPC ................ *A61B 8/543* (2013.01); *A61B 8/06* (2013.01); *A61B 8/0891* (2013.01); *A61B 8/488* (2013.01)

(58) Field of Classification Search
None
See application file for complete search history.

(56) References Cited

U.S. PATENT DOCUMENTS

| | | |
|---|---|---|
| 2001/0016686 A1 | 8/2001 | Okada et al. |
| 2008/0021318 A1 | 1/2008 | Kato et al. |

(Continued)

FOREIGN PATENT DOCUMENTS

| | | |
|---|---|---|
| JP | 2001-218768 A | 8/2001 |
| JP | 2017-524455 A | 8/2017 |

(Continued)

OTHER PUBLICATIONS

International Search Report issued in PCT/JP2020/016285; mailed Jun. 9, 2020.

(Continued)

*Primary Examiner* — Shahdeep Mohammed
(74) *Attorney, Agent, or Firm* — Studebaker Brackett PLLC

(57) ABSTRACT

An ultrasound diagnostic apparatus (1) includes a time phase search period specifying unit (16) that specifies a time phase search period in each heartbeat period on the basis of Doppler data; and a frame specifying unit (12) that specifies at least one of B-mode data of a frame with a maximum diameter of a blood vessel or B-mode data of a frame with a minimum diameter of the blood vessel in each heartbeat period by analyzing the B-mode data of a plurality of frames in the time phase search period specified by the time phase search period specifying unit (16).

16 Claims, 13 Drawing Sheets

(56)    References Cited

U.S. PATENT DOCUMENTS

| 2009/0048518 A1* | 2/2009 | Furman ................ A61B 5/0205 |
| | | 600/438 |
| 2016/0015366 A1* | 1/2016 | Haugaard ............ A61B 8/5223 |
| | | 600/447 |
| 2016/0128667 A1* | 5/2016 | Lee .................... A61B 5/02007 |
| | | 600/438 |
| 2018/0014810 A1 | 1/2018 | Chen et al. |
| 2019/0099153 A1 | 4/2019 | Weinberg |
| 2020/0245974 A1* | 8/2020 | Soroida ................ A61B 8/5207 |

FOREIGN PATENT DOCUMENTS

| WO | 2006/011504 A1 | 2/2006 |
| WO | WO 2018/164181 * | 9/2018 |

OTHER PUBLICATIONS

International Preliminary Report on Patentability and Written Opinion issued in PCT/JP2020/016285; issued Sep. 28, 2021.

* cited by examiner

TIME

BLOOD FLOW VELOCITY

BLOOD FLOW RATE:
OO ml/min

MV

ULTRASOUND DIAGNOSTIC APPARATUS, CONTROL METHOD OF ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2020/016285 filed on Apr. 13, 2020, which claims priority under 35 U.S.C. § 119(a) to Japanese Patent Application No. 2019-078241 filed on Apr. 17, 2019. The above application is hereby expressly incorporated by reference, in its entirety, into the present application.

BACKGROUND OF THE INVENTION

1. Field of the Invention

The present invention relates to an ultrasound diagnostic apparatus that acquires B-mode data and Doppler data, a control method of the ultrasound diagnostic apparatus, and a processor for the ultrasound diagnostic apparatus.

2. Description of the Related Art

In the related art, an ultrasound diagnostic apparatus has been known as an apparatus for obtaining an image of the inside of a subject. The ultrasound diagnostic apparatus generally comprises an ultrasound probe comprising a transducer array in which a plurality of elements are arranged. In a state where the ultrasound probe is in contact with a body surface of the subject, an ultrasound beam is transmitted toward the inside of the subject from the transducer array and an ultrasound echo from the subject is received by the transducer array so that element data is acquired. Further, the ultrasound diagnostic apparatus electrically processes the obtained element data to generate an ultrasound image of the corresponding site of the subject.

For example, JP2017-524455A discloses an ultrasound diagnostic apparatus that detects a blood vessel region in a Brightness mode (B-mode) image in which a blood vessel of a subject is shown, on the basis of Doppler data. The ultrasound diagnostic apparatus of JP2017-524455A segments the blood vessel in the B-mode image on the basis of the detected blood vessel region, and calculates a diameter of the segmented blood vessel on the basis of the B-mode image.

SUMMARY OF THE INVENTION

In general, the maximum diameter and the minimum diameter of a blood vessel may be measured in order to calculate an elastic index or the like indicating the elasticity of the blood vessel. In a case where the minimum diameter and the maximum diameter of the blood vessel are measured using the ultrasound diagnostic apparatus in the related art as disclosed in JP2017-524455A, it is necessary to obtain the minimum value and the maximum value by comparing the diameters of blood vessels calculated from each B-mode image of a plurality of sequentially acquired frames, and therefore, there is a problem that the burden on the ultrasound diagnostic apparatus is heavy and it takes a lot of time to calculate the minimum diameter and the maximum diameter of the blood vessel. Further, in a case where the minimum diameter and the maximum diameter of the blood vessel are to be measured on the basis of only the B-mode image, in a case where a brightness value fluctuates due to the influence of noise or the like, there is a possibility that the erroneous minimum value and maximum value are measured.

The present invention has been made in order to solve such a problem in the related art, and an object of the present invention is to provide an ultrasound diagnostic apparatus, a control method of the ultrasound diagnostic apparatus, and a processor for the ultrasound diagnostic apparatus, which can easily and accurately specify at least one of B-mode data with the maximum diameter of the blood vessel or B-mode data with the minimum diameter of the blood vessel.

In order to achieve the object, an ultrasound diagnostic apparatus according to an aspect of the present invention is an ultrasound diagnostic apparatus in which B-mode data and Doppler data of a region including a blood vessel of a subject are continuously acquired for a predetermined period, the ultrasound diagnostic apparatus comprises a time phase search period specifying unit that specifies a time phase search period in each heartbeat period on the basis of the Doppler data; and a frame specifying unit that specifies at least one of the B-mode data of a frame with a maximum diameter of the blood vessel or the B-mode data of a frame with a minimum diameter of the blood vessel in each heartbeat period by analyzing the B-mode data of a plurality of frames in the time phase search period specified by the time phase search period specifying unit.

It is preferable that the ultrasound diagnostic apparatus further comprises a blood vessel diameter calculation unit that calculates at least one of a maximum diameter or a minimum diameter of the blood vessel on the basis of at least one of the B-mode data of the frame with the maximum diameter of the blood vessel or the B-mode data of the frame with the minimum diameter of the blood vessel specified by the frame specifying unit.

It is preferable that the ultrasound diagnostic apparatus further comprises a cross-sectional area calculation unit that calculates a cross-sectional area of the blood vessel using at least one of the maximum diameter or the minimum diameter of the blood vessel calculated by the blood vessel diameter calculation unit; a Doppler processing unit that acquires the Doppler data in each heartbeat period; a blood flow velocity calculation unit that calculates a blood flow velocity on the basis of the Doppler data acquired by the Doppler processing unit; and a blood flow rate measurement unit that measures a blood flow rate on the basis of the cross-sectional area calculated by the cross-sectional area calculation unit and the blood flow velocity calculated by the blood flow velocity calculation unit.

The time phase search period specifying unit can specify a first period including a time point at which the Doppler data has a minimum value in each heartbeat period as the time phase search period, the frame specifying unit can specify the B-mode data of the frame with the minimum diameter of the blood vessel on the basis of the B-mode data of the plurality of frames in the first period, the blood vessel diameter calculation unit can calculate the minimum diameter of the blood vessel on the basis of the B-mode data of the frame with the minimum diameter of the blood vessel specified by the frame specifying unit, and the cross-sectional area calculation unit can calculate the cross-sectional area of the blood vessel using the minimum diameter of the blood vessel calculated by the blood vessel diameter calculation unit.

The time phase search period specifying unit can specify a second period including a time point at which the Doppler data has a maximum value in each heartbeat period as the time phase search period, the frame specifying unit can specify the B-mode data of the frame with the maximum diameter of the blood vessel on the basis of the B-mode data of the plurality of frames in the second period, the blood vessel diameter calculation unit can calculate the maximum diameter of the blood vessel on the basis of the B-mode data of the frame with the maximum diameter of the blood vessel specified by the frame specifying unit, and the cross-sectional area calculation unit can calculate the cross-sectional area of the blood vessel using the maximum diameter of the blood vessel calculated by the blood vessel diameter calculation unit.

Moreover, the time phase search period specifying unit can specify the time phase search period having a first period including a time point at which the Doppler data has a minimum value in each heartbeat period and a second period including a time point at which the Doppler data has a maximum value in each heartbeat period, the frame specifying unit can specify the B-mode data of the frame with the minimum diameter of the blood vessel on the basis of the B-mode data of the plurality of frames in the first period, and specifies the B-mode data of the frame with the maximum diameter of the blood vessel on the basis of the B-mode data of the plurality of frames in the second period, the blood vessel diameter calculation unit can calculate the minimum diameter of the blood vessel on the basis of the B-mode data of the frame with the minimum diameter of the blood vessel specified by the frame specifying unit, and calculates the maximum diameter of the blood vessel on the basis of the B-mode data of the frame with the maximum diameter of the blood vessel specified by the frame specifying unit, and the cross-sectional area calculation unit can calculate the cross-sectional area of the blood vessel using an average diameter of the blood vessel in each heartbeat period calculated from the minimum diameter of the blood vessel and the maximum diameter of the blood vessel calculated by the blood vessel diameter calculation unit.

It is preferable that the first period is a period from the time point at which the Doppler data has the minimum value to the time point at which the Doppler data has the maximum value in each heartbeat period.

It is preferable that the second period is a period from a time point at which the Doppler data has the maximum value to a time point at which a predetermined time set to a time shorter than each heartbeat period is elapsed.

Further, it is preferable that each of the first period and the second period has a time width of 10% or more and 20% or less of each heartbeat period.

The ultrasound diagnostic apparatus may further comprise an elastic index calculation unit that calculates an elastic index of the blood vessel on the basis of a difference between the maximum diameter of the blood vessel and the minimum diameter of the blood vessel.

It is preferable that the ultrasound beam further comprises an ultrasound probe; a transmission and reception circuit that transmits an ultrasound beam to an inside of the subject via the ultrasound probe, and receives an ultrasound echo from the inside of the subject to generate reception data; and a B-mode processing unit that generates the B-mode data on the basis of the reception data generated by the transmission and reception circuit.

A control method of an ultrasound diagnostic apparatus according to another aspect of the present invention is a control method of an ultrasound diagnostic apparatus in which B-mode data and Doppler data of a region including a blood vessel of a subject are continuously acquired for a predetermined period, and the control method includes specifying a time phase search period in each heartbeat period on the basis of the Doppler data; and specifying at least one of the B-mode data of a frame with a maximum diameter of the blood vessel or the B-mode data of a frame with a minimum diameter of the blood vessel in each heartbeat period by analyzing the B-mode data of a plurality of frames in the specified time phase search period.

A processor for an ultrasound diagnostic apparatus according to still another aspect of the present invention is a processor for an ultrasound diagnostic apparatus, and the processor includes acquiring B-mode data and Doppler data of a region including a blood vessel of a subject continuously for a predetermined period; specifying a time phase search period in each heartbeat period on the basis of the Doppler data; and specifying at least one of the B-mode data of a frame with a maximum diameter of the blood vessel or the B-mode data of a frame with a minimum diameter of the blood vessel in each heartbeat period by analyzing the B-mode data of a plurality of frames in the specified time phase search period.

According to the present invention, since there are provided a time phase search period specifying unit that specifies a time phase search period in each heartbeat period on the basis of Doppler data; and a frame specifying unit that specifies at least one of B-mode data of a frame with a maximum diameter of a blood vessel or B-mode data of a frame with a minimum diameter of the blood vessel in each heartbeat period by analyzing the B-mode data of a plurality of frames in the time phase search period specified by the time phase search period specifying unit, at least one of the B-mode data with the maximum diameter of the blood vessel or the B-mode data with the minimum diameter of the blood vessel can be easily and accurately specified.

BRIEF DESCRIPTION OF THE DRAWINGS

FIG. 11 is a diagram schematically illustrating the B-mode image and the Doppler waveform image displayed on a display device in the first embodiment of the present invention.

FIG. 12 is a diagram schematically illustrating the B-mode image, the Doppler waveform image, and a measurement value of a blood flow rate displayed on the display device in the first embodiment of the present invention.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In addition, in the present specification, the terms "perpendicular" and "parallel" include a range of errors allowed in the technical field to which the present invention belongs. For example, the terms "perpendicular" and "parallel" mean a range less than ±10° with respect to the strict perpendicular or parallel, and the error with respect to the strict perpendicular or parallel is preferably 5° or less, and more preferably 3° or less.

In the present specification, the terms "same" and "identical" include an error range generally allowed in the technical field. Further, in the present specification, in a case of referring to "all", "any", or "whole surface", the term includes an error range generally allowed in the technical field in addition to a case of 100%, and includes, for example, a case of 99% or more, a case of 95% or more, or a case of 90% or more.

First Embodiment

Figure 1:
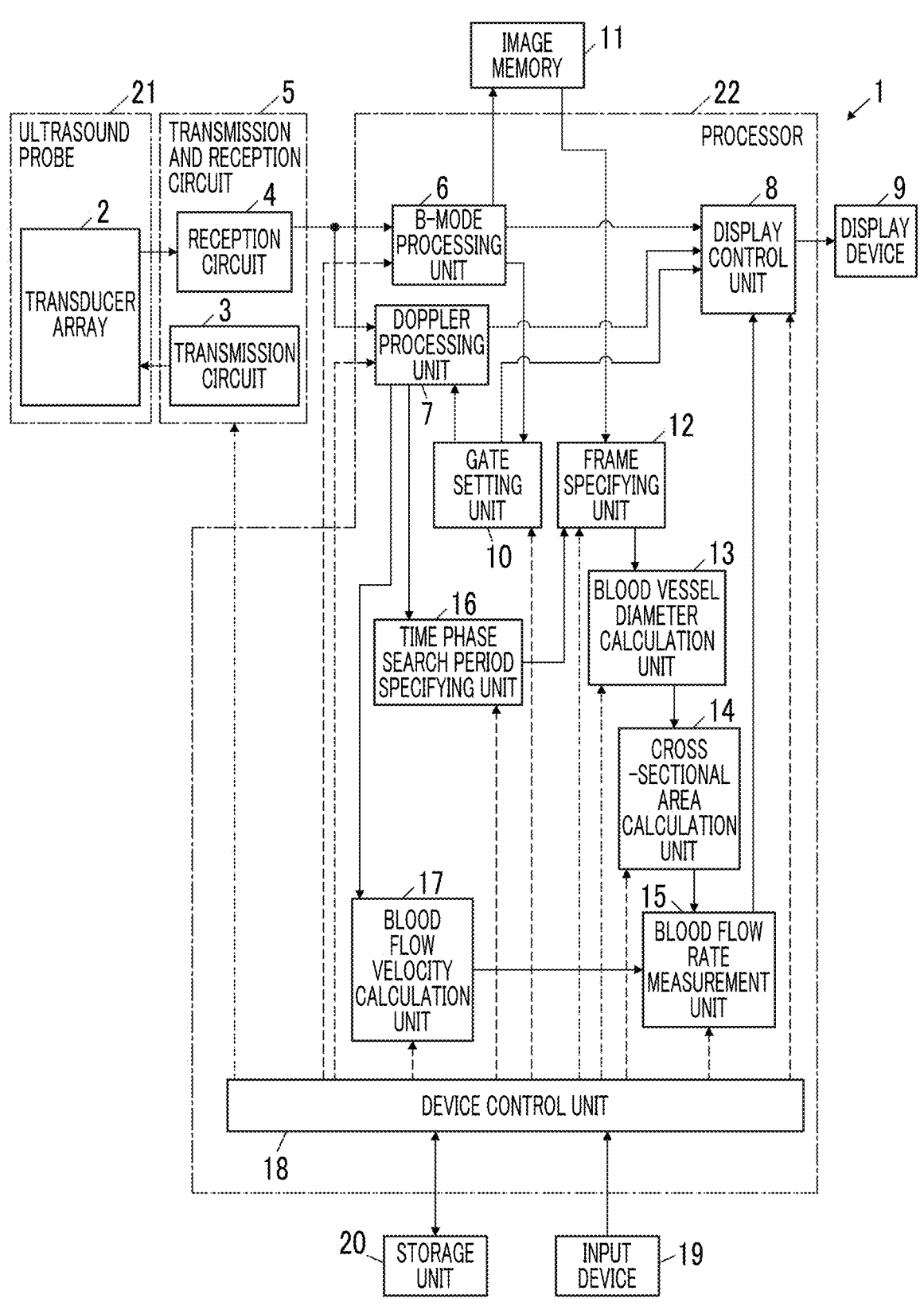
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. As illustrated in FIG. 1, the ultrasound diagnostic apparatus 1 comprises a transducer array 2, and each of a transmission circuit 3 and a reception circuit 4 is connected to the transducer array 2. Here, the transmission circuit 3 and the reception circuit 4 constitute a transmission and reception circuit 5. A Brightness mode (B-mode) processing unit 6 and a Doppler processing unit 7 are connected to the reception circuit 4, and a display device 9 is connected to the B-mode processing unit 6 and the Doppler processing unit 7 via a display control unit 8.

A gate setting unit 10 is connected to the B-mode processing unit 6, and the Doppler processing unit 7 and the display control unit 8 are connected to the gate setting unit 10. An image memory 11 is connected to the B-mode processing unit 6, and a frame specifying unit 12 is connected to the image memory 11. A blood vessel diameter calculation unit 13, a cross-sectional area calculation unit 14, and a blood flow rate measurement unit 15 are sequentially connected to the frame specifying unit 12. A time phase search period specifying unit 16 and a blood flow velocity calculation unit 17 are connected to the Doppler processing unit 7. The frame specifying unit 12 is connected to the time phase search period specifying unit 16, and the blood flow rate measurement unit 15 is connected to the blood flow velocity calculation unit 17.

In addition, a device control unit 18 is connected to the transmission and reception circuit 5, the B-mode processing unit 6, the Doppler processing unit 7, the display control unit 8, the gate setting unit 10, the frame specifying unit 12, the blood vessel diameter calculation unit 13, the cross-sectional area calculation unit 14, the blood flow rate measurement unit 15, the time phase search period specifying unit 16, and the blood flow velocity calculation unit 17, and an input device 19 and a storage unit 20 are connected to the device control unit 18. The device control unit 18 and the storage unit 20 are connected so as to exchange information bidirectionally.

Further, the transducer array 2 is included in an ultrasound probe 21, and the B-mode processing unit 6, the Doppler processing unit 7, the display control unit 8, the gate setting unit 10, the frame specifying unit 12, the blood vessel diameter calculation unit 13, the cross-sectional area calculation unit 14, the blood flow rate measurement unit 15, the time phase search period specifying unit 16, the blood flow velocity calculation unit 17, and the device control unit 18 constitute a processor 22 for the ultrasound diagnostic apparatus 1.

The transducer array 2 of the ultrasound probe 21 illustrated in FIG. 1 has a plurality of transducers arranged in a one-dimensional or two-dimensional manner. According to a drive signal supplied from the transmission circuit 3, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 includes, for example, a plurality of pulse generators, and the transmission circuit 3 adjusts the amount of delay of each drive signal so that ultrasonic waves transmitted from the plurality of transducers of the transducer array 2 form an ultrasound beam on the basis of a transmission delay pattern selected according to the control signal from the device control unit 18, and supplies the obtained signals to the plurality of transducers. Thus, in a case where a pulsed or continuous-wave voltage is applied to the electrodes of the transducers of the transducer array 2, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 2 of the ultrasound probe 21. The ultrasonic waves propagating toward the transducer array 2 in this manner are received by each transducer constituting the transducer array 2. In this case, each transducer constituting the transducer array 2 expands and contracts by receiving the propagating ultrasound echo to generate electrical signals, and outputs the electrical signals to the reception circuit 4.

Figure 2:
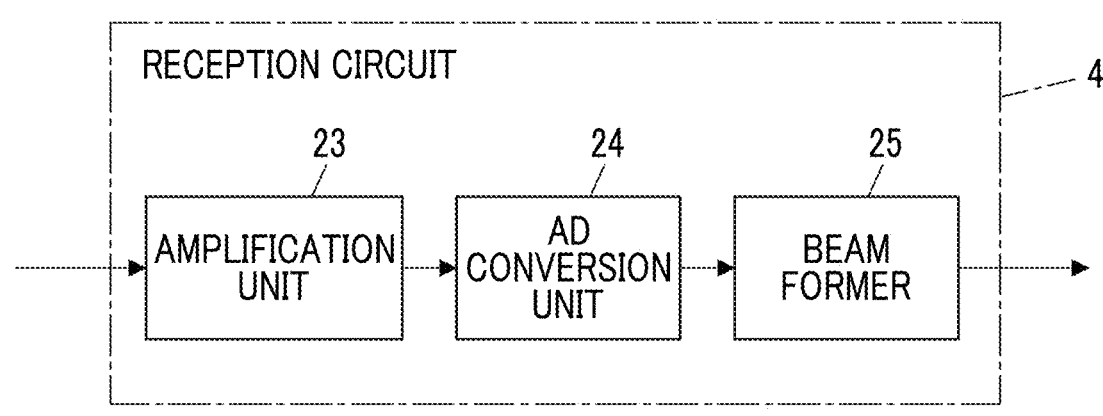
FIG. 2 is a block diagram illustrating an internal configuration of a reception circuit in the first embodiment of the present invention.

The reception circuit 4 performs processing on the signals output from the transducer array 2 according to the control signal from the device control unit 18 to generate reception data, which is so-called radio frequency (RF) data. As illustrated in FIG. 2, the reception circuit 4 has a configuration in which an amplification unit 23, an analog digital (AD) conversion unit 24, and a beam former 25 are connected in series.

The amplification unit 23 amplifies the signals input from each transducer constituting the transducer array 2, and transmits the amplified signals to the AD conversion unit 24. The AD conversion unit 24 converts the signals transmitted from the amplification unit 23 into digital data, and transmits the data to the beam former 25. The beam former 25 performs so-called reception focusing processing in which addition is performed by giving delays to respective pieces of data converted by the AD conversion unit 24 according to a sound speed distribution or a sound speed set on the basis of a reception delay pattern selected according to the control signals from the device control unit 18. Through the reception focusing processing, reception data in which each piece of data converted by the AD conversion unit 24 is phased and added and the focus of the ultrasound echo is narrowed is acquired.

Figure 3:
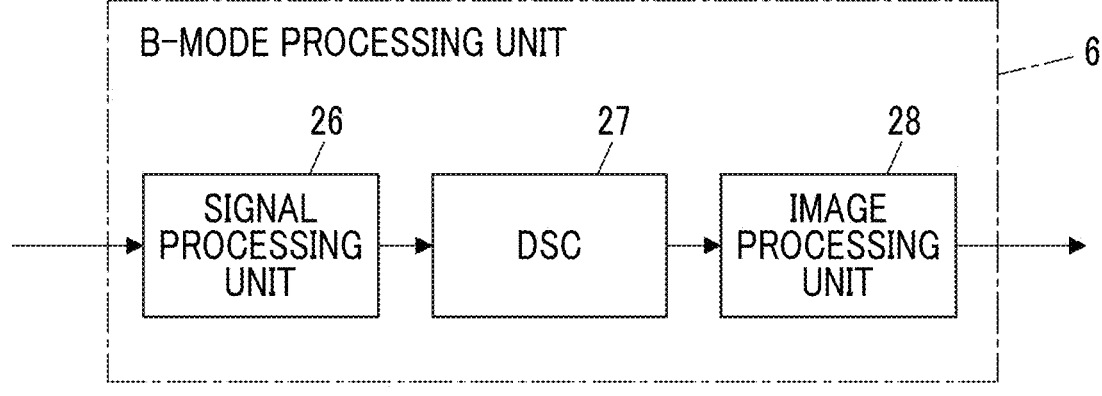
FIG. 3 is a block diagram illustrating an internal configuration of a B-mode processing unit in the first embodiment of the present invention.

As illustrated in FIG. 3, the B-mode processing unit 6 has a configuration in which a signal processing unit 26, a digital scan converter (DSC) 27, and an image processing unit 28 are sequentially connected in series.

The signal processing unit 26 generates a B-mode image signal, which is tomographic image information regarding tissues inside the subject, by performing, on reception data generated by the reception circuit 4, correction of the attenuation due to the distance according to the depth of the reflection position of the ultrasonic wave and then performing envelope detection processing.

The DSC 27 converts (raster conversion) the B-mode image signal generated by the signal processing unit 26 into an image signal according to a normal television signal scanning method.

The image processing unit 28 performs various kinds of necessary image processing such as gradation processing on the B-mode image signal input from the DSC 27, and then outputs the B-mode image signal to the display control unit 8.

Figure 4:
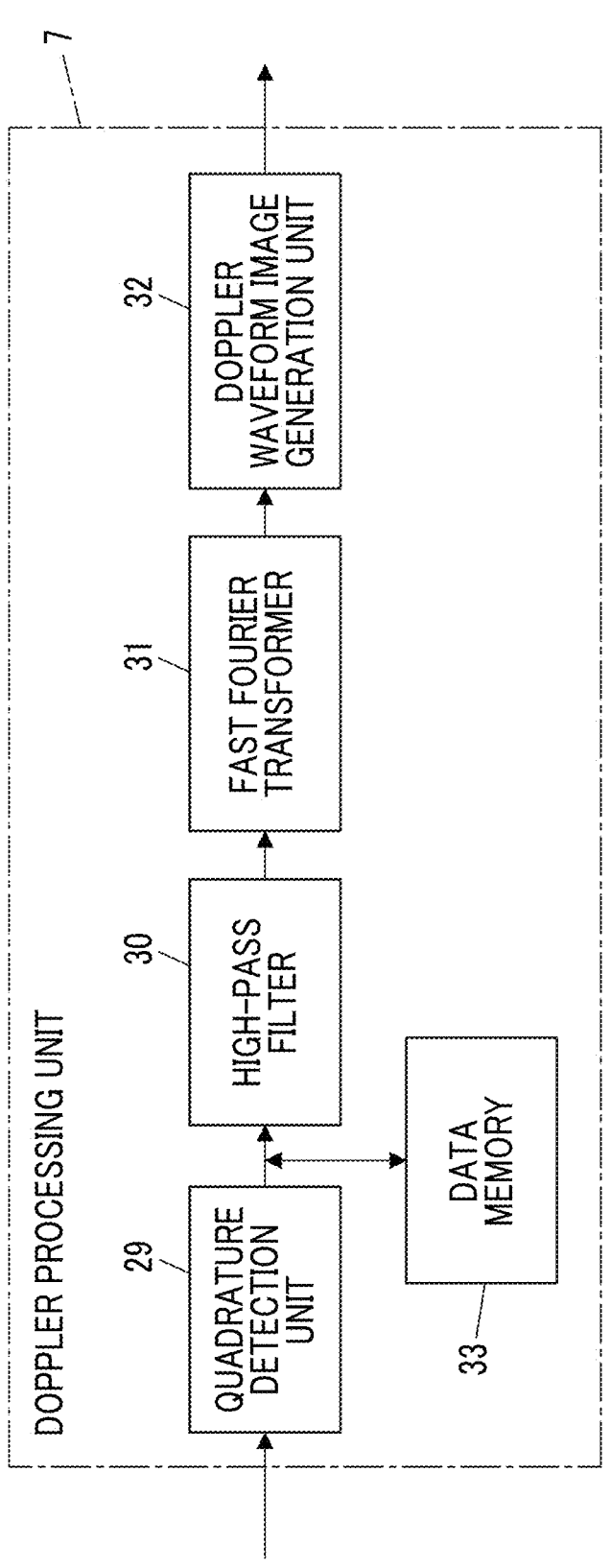
FIG. 4 is a block diagram illustrating an internal configuration of a Doppler processing unit in the first embodiment of the present invention.

The Doppler processing unit 7 acquires Doppler data in the Doppler gate set in a blood vessel region by the gate setting unit 10, which will be described later, to generate a Doppler waveform image. As illustrated in FIG. 4, the Doppler processing unit 7 has a configuration in which a quadrature detection unit 29, a high-pass filter 30, a fast Fourier transformer 31, and a Doppler waveform image generation unit 32 are sequentially connected in series and a data memory 33 is connected to an output terminal of the quadrature detection unit 29.

The quadrature detection unit 29 mixes the reception data generated by the reception circuit 4 with a carrier signal having a reference frequency to perform quadrature detection on the reception data and converts the reception data into complex data.

The high-pass filter 30 functions as a so-called wall filter, and removes a frequency component derived from the motion of the body tissue inside the subject, from the complex data generated by the quadrature detection unit 29.

The fast Fourier transformer 31 performs a Fourier transform on the complex data of a plurality of sample points to perform frequency analysis, obtains the blood flow velocity, and generates a spectrum signal.

Figure 5:
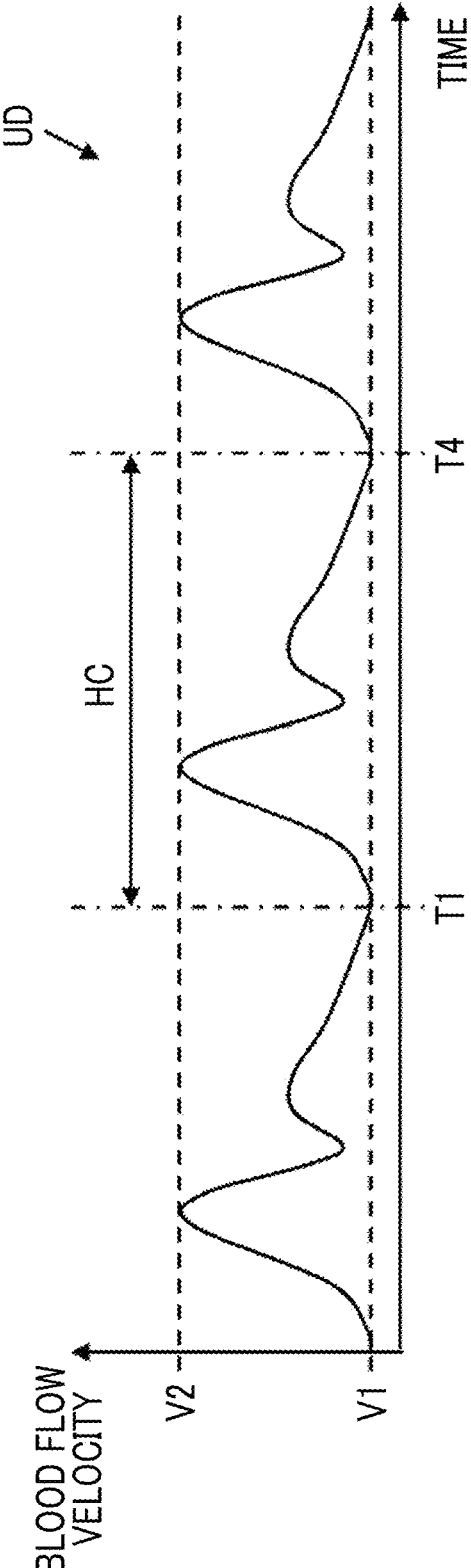
FIG. 5 is a diagram schematically illustrating a Doppler waveform image in the first embodiment of the present invention.

The Doppler waveform image generation unit 32 generates a Doppler waveform image signal by aligning the spectrum signals generated by the fast Fourier transformer 31 on a time axis and expressing the magnitude of each frequency component in brightness. Here, FIG. 5 illustrates an example of an ideal Doppler waveform image UD based on the Doppler waveform image signal. In the Doppler waveform image UD, the lateral axis indicates a time axis, the vertical axis indicates a Doppler shift frequency, that is, a blood flow velocity, and the brightness of the waveform represents power in each frequency component. The value of the blood flow velocity in the Doppler waveform image UD is changed periodically according to a heartbeat period HC. Regarding the heartbeat period HC, a period from a time point T1 at which the blood flow velocity has a minimum value V1 to a time point T4 at which the blood flow velocity has the next minimum value V1 is defined as the heartbeat period HC.

Further, the data memory 33 saves the complex data converted from the reception data by the quadrature detection unit 29.

The device control unit 18 controls each unit of the ultrasound diagnostic apparatus 1 on the basis of a program stored in advance in the storage unit 20 or the like and the user's input operation through the input device 19.

The display control unit 8 performs predetermined processing on the B-mode image signal generated by the B-mode processing unit 6 and the Doppler waveform image signal generated by the Doppler processing unit 7, and causes the display device 9 to display the B-mode image and the Doppler waveform image, under the control of the device control unit 18.

The display device 9 of the ultrasound diagnostic apparatus 1 is for displaying the image generated by the display control unit 8, and includes a display device such as a liquid crystal display (LCD), or an organic electroluminescence (EL) display.

The input device 19 of the ultrasound diagnostic apparatus 1 is for the user to perform an input operation, and can be configured to comprise a keyboard, a mouse, a trackball, a touchpad, a touch panel, and the like.

Figure 6:
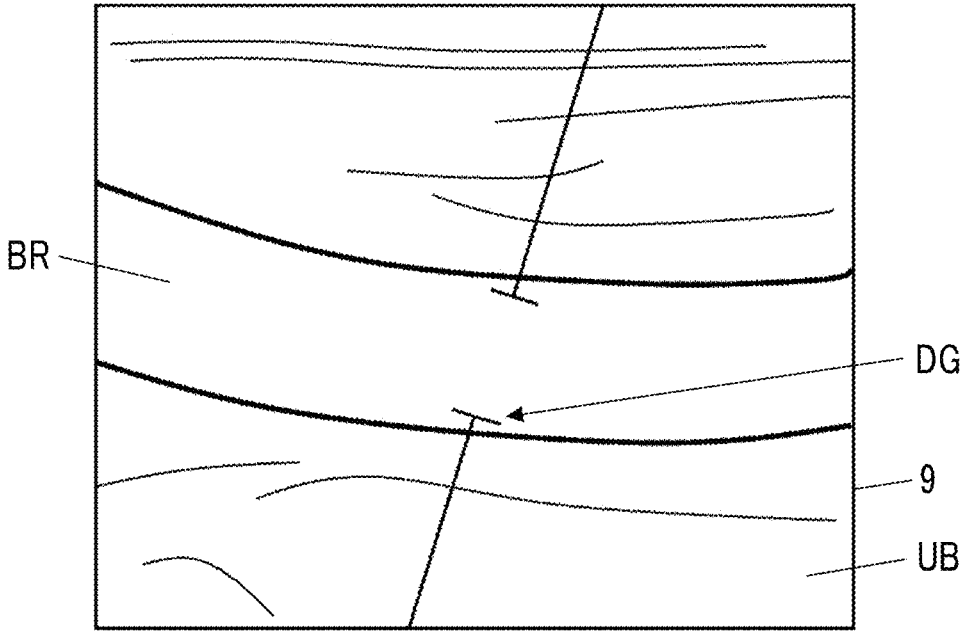
FIG. 6 is a diagram schematically illustrating an example of a B-mode image in which a Doppler gate is set in the first embodiment of the present invention.

As illustrated in FIG. 6, the gate setting unit 10 sets a Doppler gate DG in a blood vessel region BR on a B-mode image UB on the basis of the user's input operation through the input device 19. For example, in a case where the user designates an appropriate position in the blood vessel region BR on the B-mode image UB through the input device 19 while watching the B-mode image UB displayed on the display device 9, the gate setting unit 10 disposes the Doppler gate DG at the position designated by the user. The Doppler gate DG set in this manner is superimposed on the B-mode image UB and is displayed on the display device 9.

The Doppler processing unit 7 acquires Doppler data in the Doppler gate DG set by the gate setting unit 10.

In general, in a case where the minimum diameter and the maximum diameter of the blood vessel in the subject are calculated using the ultrasound diagnostic apparatus, it is necessary to compare the diameters of the blood vessel for all of the B-mode images of a plurality of continuously generated frames over each heartbeat period HC. Therefore, in a case where the minimum diameter and the maximum diameter of the blood vessel are calculated, there is a problem that the burden on the ultrasound diagnostic apparatus is heavy and it takes a lot of time.

Figure 7:
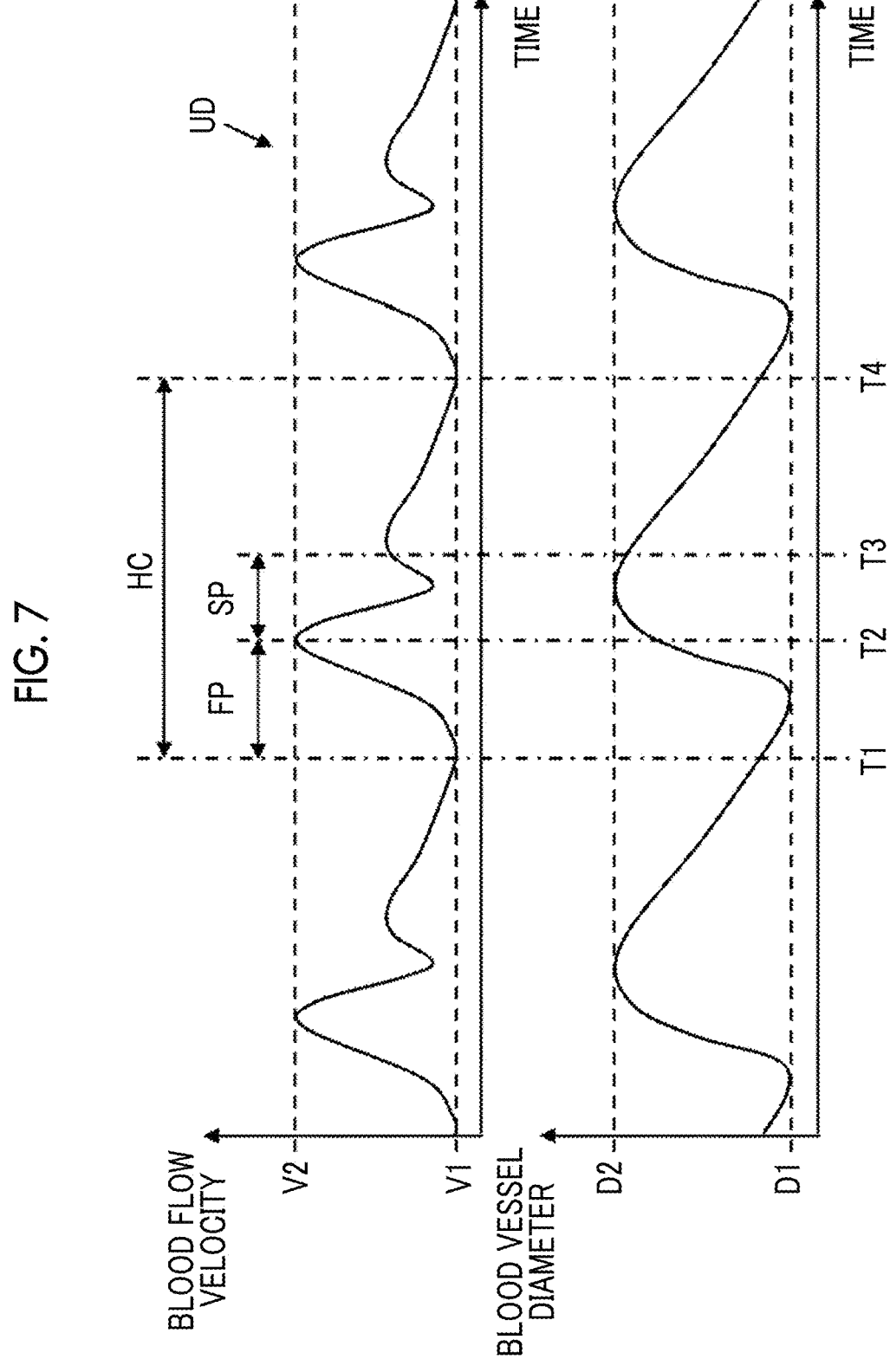
FIG. 7 is a diagram schematically illustrating a relationship between an ideal Doppler waveform image and an ideal time change of a blood vessel diameter in the first embodiment of the present invention.

The present inventors have found the relationship as illustrated in FIG. 7 by focusing on a time change of the blood flow velocity and a time change of the diameter of the blood vessel in the Doppler waveform image UD. Similar to the blood flow velocity, the diameter of the blood vessel is changed periodically between a minimum value D1 and a maximum value D2 according to the heartbeat period HC, but the diameter of the blood vessel has the minimum value V1 in a period including the time point T1 at which the blood flow velocity has the minimum value V1, that is, a first period FP from the time point T1 at which the blood flow velocity has the minimum value V1 to a time point T2 at which the blood flow velocity has a maximum value V2. Further, the diameter of the blood vessel has the maximum value D2 in a period including the time point T2 at which the blood flow velocity has the maximum value V2, that is, a second period SP from the time point T2 at which the blood flow velocity has the maximum value V2 to a time point T3 after a predetermined time set to a time shorter than each heartbeat period HC, for example, 0.25 seconds or the like has elapsed from the time point T2.

Therefore, by specifying the first period FP and the second period SP, the burden on the ultrasound diagnostic apparatus 1 can be reduced, and the B-mode image in which the diameter of the blood vessel has the minimum value D1 and the B-mode image in which the diameter of the blood vessel has the maximum value D2 can be easily specified in a short time. Further, in a case where the B-mode image in which the diameter of the blood vessel has the minimum value D1 and the B-mode image in which the diameter of the blood vessel has the maximum value D2 are specified, the diameters of the blood vessels in the B-mode images in the first period FP and the second period SP may be compared with each other, and it is possible to reduce a possibility that the B-mode image in which the brightness value fluctuates due to the influence of noise or the like is erroneously specified.

The time phase search period specifying unit 16 specifies at least one of the first period FP or the second period SP in each heartbeat period HC as a time phase search period on the basis of the Doppler data generated by the Doppler processing unit 7. Here, the time phase search period is a period for specifying at least one of the B-mode image signal with the maximum diameter of the blood vessel or the B-mode image signal with the minimum diameter of the blood vessel in each heartbeat period HC.

Figure 8:
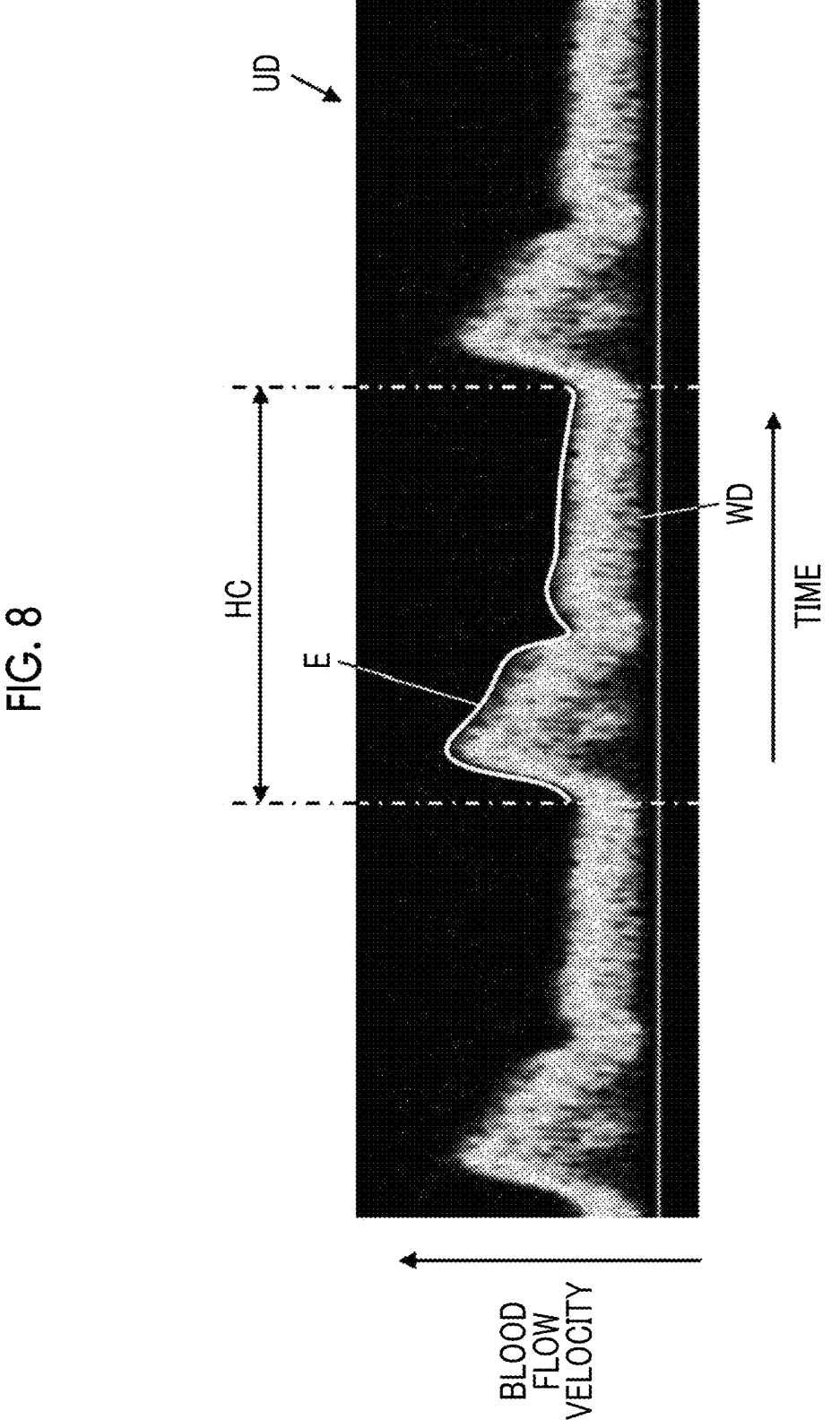
FIG. 8 is a diagram illustrating an example of an actual Doppler waveform image in the first embodiment of the present invention.

As illustrated in FIG. 8, the time phase search period specifying unit 16 sets an envelope curve E of a Doppler waveform WD in each heartbeat period HC, and specifies the time phase search period on the basis of the set envelope curve E.

The image memory 11 is a memory that saves the B-mode image signals of the plurality of frames continuously generated by the B-mode processing unit 6. Here, as the image memory 11, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The frame specifying unit 12 analyzes the B-mode image signals of the plurality of frames in the time phase search period specified by the time phase search period specifying unit 16, among the B-mode image signals of the plurality of frames saved in the image memory 11, and specifies at least one of the B-mode image signal of the frame with the maximum diameter of the blood vessel or the B-mode image signal of the frame with the minimum diameter of the blood vessel in each heartbeat period HC. In this case, the frame specifying unit 12 can calculate the diameter of the blood vessel in the B-mode image signal of each frame in the time phase search period, for example, and specify at least one of the B-mode image signal of the frame with the maximum diameter of the blood vessel or the B-mode image signal of the frame with the minimum diameter of the blood vessel on the basis of the calculated diameter of the blood vessel.

Figure 9:
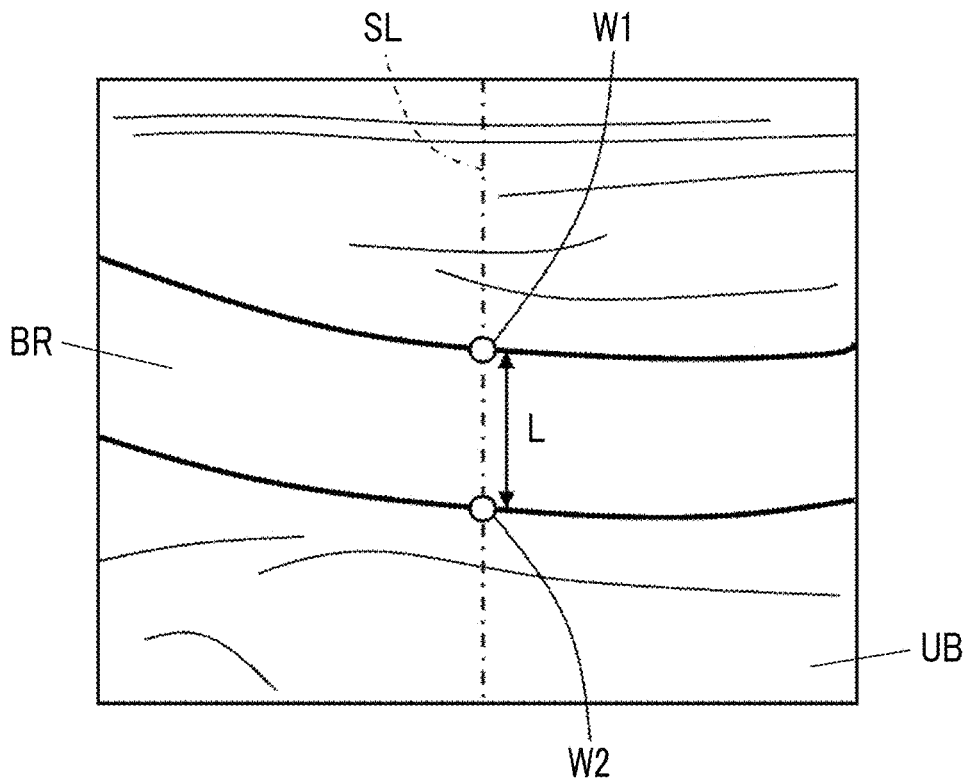
FIG. 9 is a diagram schematically illustrating a method of calculating a blood vessel diameter in the first embodiment of the present invention.

In a case where the frame specifying unit 12 calculates the diameter of the blood vessel in the B-mode image signal of each frame, for example, as illustrated in FIG. 9, the frame specifying unit 12 can specify positions of two points where the brightness of the B-mode image UB is higher than a certain value, on a straight line SL in a vertical direction set on the B-mode image UB by the user's input operation or the like through the input device 19, as a position of an anterior vascular wall W1 and a position of a posterior vascular wall W2, and can calculate a distance L between the specified two points on the B-mode image UB. For example, as the straight line SL, a perpendicular line passing through the center of the B-mode image UB may be used.

The frame specifying unit 12 specifies the B-mode image signal of the frame with the minimum diameter of the blood vessel calculated in this manner, in the first period FP of the time phase search period. Further, the frame specifying unit 12 specifies the B-mode image signal of the frame with the maximum diameter of the blood vessel calculated in this manner, in the second period SP of the time phase search period.

The blood vessel diameter calculation unit 13 calculates at least one of the maximum diameter or the minimum diameter of the blood vessel on the basis of at least one of the B-mode image signal of the frame with the minimum diameter of the blood vessel or the B-mode image signal of the frame with the maximum diameter of the blood vessel specified by the frame specifying unit 12. For example, the blood vessel diameter calculation unit 13 can calculate the maximum diameter of the blood vessel by converting the distance L on the B-mode image UB calculated as the diameter of the blood vessel by the frame specifying unit 12, in the B-mode image signal of the frame with the maximum diameter of the blood vessel, into the actual diameter of the blood vessel. For example, the blood vessel diameter calculation unit 13 can calculate the minimum diameter of the blood vessel on the basis of the distance L on the B-mode image UB calculated as the diameter of the blood vessel by the frame specifying unit 12, in the B-mode image signal of the frame with the minimum diameter of the blood vessel.

The cross-sectional area calculation unit 14 calculates a cross-sectional area of the blood vessel on the basis of the diameter of the blood vessel calculated by the blood vessel diameter calculation unit 13, assuming that the blood vessel has a circular cross section. For example, in a case where the minimum diameter of the blood vessel is calculated by the blood vessel diameter calculation unit 13, the cross-sectional area calculation unit 14 calculates the cross-sectional area of the blood vessel using the minimum diameter of the blood vessel. Further, for example, in a case where the maximum diameter of the blood vessel is calculated by the blood vessel diameter calculation unit 13, the cross-sectional area calculation unit 14 calculates the cross-sectional area of the blood vessel using the maximum diameter of the blood vessel. Further, for example, in a case where both the minimum diameter and the maximum diameter of the blood vessel are calculated by the blood vessel diameter calculation unit 13, the cross-sectional area calculation unit 14 can calculate the average diameter of the blood vessel on the basis of the minimum diameter and the maximum diameter of the blood vessel, and calculate the cross-sectional area of the blood vessel using the calculated average diameter of the blood vessel.

The blood flow velocity calculation unit 17 calculates the blood flow velocity by a so-called pulse Doppler method on the basis of the Doppler data acquired by the Doppler processing unit 7. The blood flow velocity calculation unit 17 can calculate an average blood flow velocity in each heartbeat period HC.

The blood flow rate measurement unit 15 measures a blood flow rate representing the volume of the blood flowing in the blood vessel per unit time on the basis of the cross-sectional area of the blood vessel calculated by the cross-sectional area calculation unit 14 and the average blood flow velocity calculated by the average blood flow velocity calculation unit 17.

The storage unit 20 stores an operation program and the like of the ultrasound diagnostic apparatus 1, and recording media such as a flash memory, an HDD, an SSD, an FD, an MO disc, an MT, a RAM, a CD, a DVD, an SD card, and an USB memory, a server, or the like can be used as the storage unit 20.

The processor 22 having the B-mode processing unit 6, the Doppler processing unit 7, the display control unit 8, the gate setting unit 10, the frame specifying unit 12, the blood vessel diameter calculation unit 13, the cross-sectional area calculation unit 14, the blood flow rate measurement unit 15, the time phase search period specifying unit 16, the blood flow velocity calculation unit 17, and the device control unit 18 is configured by a central processing unit (CPU) and a control program for causing the CPU to execute various kinds of processing, but the processor 22 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the B-mode processing unit 6, the Doppler processing unit 7, the display control unit 8, the gate setting unit 10, the frame specifying unit 12, the blood vessel diameter calculation unit 13, the cross-sectional area calculation unit 14, the blood flow rate measurement unit 15, the time phase search period specifying unit 16, the blood flow velocity calculation unit 17, and the device control unit 18 of the processor 22 can also be configured by being integrated partially or entirely into one CPU or the like.

Next, the operation of the ultrasound diagnostic apparatus 1 in the first embodiment will be described in detail using the flowchart illustrated in FIG. 10.

In Step S1, as illustrated in FIG. 6, the Doppler gate DG is set on the B-mode image UB by the gate setting unit 10 on the basis of the user's input operation through the input device 19.

Figure 11:
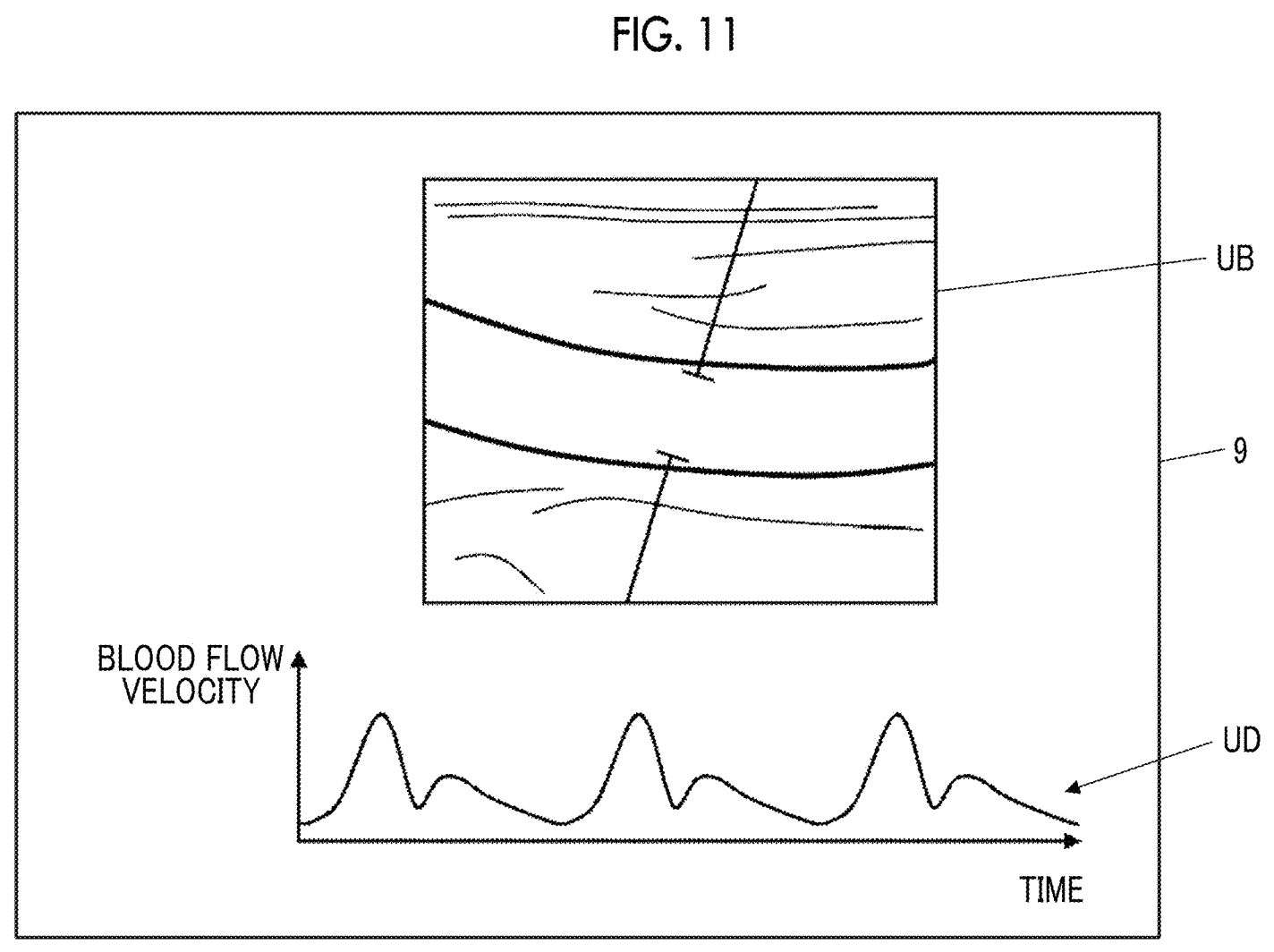

Next, in Step S2, the B-mode image signal and the Doppler waveform image signal are generated for a set period longer than the heartbeat period HC by the B-mode processing unit 6 and the Doppler processing unit 7. In this case, the B-mode processing unit 6 sequentially and continuously generates the B-mode image signals in which at least the blood vessel region BR is imaged, and causes the display device 9 to display the B-mode image UB based on the generated B-mode image signals. Further, the Doppler processing unit 7 acquires the Doppler data in the Doppler gate DG set in Step S1, sequentially and continuously generates the Doppler waveform image signals on the basis of the acquired Doppler data, and causes the display device 9 to display the Doppler waveform image UD based on the generated Doppler waveform image signals. Thereby, for example, as illustrated in FIG. 11, the B-mode image UB and the Doppler waveform image UD are displayed on the display device 9. The B-mode image signals of the plurality of frames generated in Step S2 are saved in the image memory 11.

In subsequent Step S3, the time phase search period specifying unit 16 specifies the time phase search period on the basis of the Doppler waveform image UD generated in Step S2. In this case, as illustrated in FIG. 7, the time phase search period specifying unit 16 specifies, as the time phase search period, at least one of the first period FP from the time point T1 at which the blood flow velocity in the Doppler waveform image UD has the minimum value V1 to the time point T2 at which the blood flow velocity has the maximum value V2 or the second period SP from the time point T2 at which the blood flow velocity has the maximum value V2 to the time point T3 after a predetermined time set to a time shorter than each heartbeat period HC, for example, 0.25 seconds or the like has elapsed from the time point T2. As illustrated in FIG. 7, in the first period FP, the diameter of the blood vessel has the minimum value D1, and in the second period SP, the diameter of the blood vessel has the maximum value D2.

In Step S4, the frame specifying unit 12 analyzes the B-mode image signals of the plurality of frames in the time phase search period specified in Step S3, among the B-mode image signals of the plurality of frames generated in Step S2, and specifies at least one of the B-mode image signal of the frame with the maximum diameter of the blood vessel or the B-mode image signal of the frame with the minimum diameter of the blood vessel in each heartbeat period HC.

For example, in a case where the first period FP is specified as the time phase search period in Step S3, the frame specifying unit 12 detects the vascular wall in the B-mode image signals of the plurality of frames in the first period FP, calculates the diameter of the blood vessel on the basis of the detected vascular wall, and specifies the B-mode image signal of the frame in which the calculated diameter of the blood vessel has the minimum value D1.

Here, in a case where the frame specifying unit 12 calculates the diameter of the blood vessel in the B-mode image signal of each frame, for example, as illustrated in FIG. 9, the frame specifying unit 12 can specify positions of two points where the brightness of the B-mode image UB is higher than a certain value, on the straight line SL in the vertical direction set on the B-mode image UB by the user's input operation or the like through the input device 19, as the position of the anterior vascular wall W1 and the position of the posterior vascular wall W2, and can calculate the distance L between the specified two points on the B-mode image UB.

Further, for example, in a case where the second period SP is specified as the time phase search period in Step S3, the frame specifying unit 12 detects the vascular wall in the B-mode image signals of the plurality of frames in the second period SP, calculates the diameter of the blood vessel on the basis of the detected vascular wall, and specifies the B-mode image signal of the frame in which the calculated diameter of the blood vessel has the maximum value D2.

In a case where both the first period FP and the second period SP are specified as the time phase search period in Step S3, the frame specifying unit 12 specifies the B-mode image signal of the frame in which the diameter of the blood vessel has the minimum value D1 in the first period FP, and specifies the B-mode image signal of the frame in which the diameter of the blood vessel has the maximum value D2 in the second period SP.

Thus, since the frame specifying unit 12 specifies at least one of the B-mode image signal of the frame with the minimum diameter of the blood vessel or the B-mode image signal of the frame with the maximum diameter of the blood vessel in the time phase search period specified in Step S3, the burden on the ultrasound diagnostic apparatus 1 can be reduced, and at least one of the B-mode image signal of the frame with the minimum diameter of the blood vessel or the B-mode image signal of the frame with the maximum diameter of the blood vessel can be easily specified in a short time. It is possible to reduce a possibility that the frame specifying unit 12 erroneously specifies the B-mode image signal in which the brightness value fluctuates due to the influence of noise or the like.

In Step S5, the blood vessel diameter calculation unit 13 calculates at least one of the maximum diameter or the minimum diameter of the blood vessel on the basis of at least one of the B-mode image signal of the frame with the minimum diameter of the blood vessel or the B-mode image signal of the frame with the maximum diameter of the blood vessel specified in Step S4. For example, in a case where the first period FP is specified as the time phase search period in Step S3 and the B-mode image signal of the frame with the minimum diameter of the blood vessel is specified in Step S4, the blood vessel diameter calculation unit 13 can calculate the minimum diameter of the blood vessel by converting the distance L on the B-mode image UB calculated as the diameter of the blood vessel in Step S4, in the B-mode image signal of the frame with the minimum diameter of the blood vessel, into the actual diameter of the blood vessel.

Further, for example, in a case where the second period SP is specified as the time phase search period in Step S3 and the B-mode image signal of the frame with the maximum diameter of the blood vessel is specified in Step S4, the blood vessel diameter calculation unit 13 can calculate the maximum diameter of the blood vessel by converting the distance L on the B-mode image UB calculated as the diameter of the blood vessel in Step S4, in the B-mode image signal of the frame with the maximum diameter of the blood vessel, into the actual diameter of the blood vessel.

For example, in a case where both the first period FP and the second period SP are specified as the time phase search period in Step S3 and both the B-mode image signal of the frame with the minimum diameter of the blood vessel and the B-mode image signal of the frame with the maximum diameter of the blood vessel are specified in Step S4, the blood vessel diameter calculation unit 13 can calculate both the minimum diameter and the maximum diameter of the blood vessel.

In Step S6, the cross-sectional area calculation unit 14 calculates the cross-sectional area of the blood vessel using at least one of the minimum diameter or the maximum diameter of the blood vessel calculated in Step S5, assuming that the blood vessel has a circular cross section. For example, in a case where the minimum diameter of the blood vessel is calculated in Step S5, the cross-sectional area calculation unit 14 calculates the cross-sectional area of the blood vessel using the minimum diameter of the blood vessel. Further, for example, in a case where the maximum diameter of the blood vessel is calculated in Step S5, the cross-sectional area calculation unit 14 calculates the cross-sectional area of the blood vessel using the maximum diameter of the blood vessel. Further, for example, in a case where both the minimum diameter and the maximum diameter of the blood vessel are calculated in Step S5, the cross-sectional area calculation unit 14 can calculate an average diameter of the blood vessel on the basis of the minimum diameter and the maximum diameter of the blood vessel, and calculate the cross-sectional area of the blood vessel using the calculated average diameter of the blood vessel.

In Step S7, the blood flow velocity calculation unit 17 calculates the blood flow velocity on the basis of the Doppler data generated in Step S2.

Figure 12:
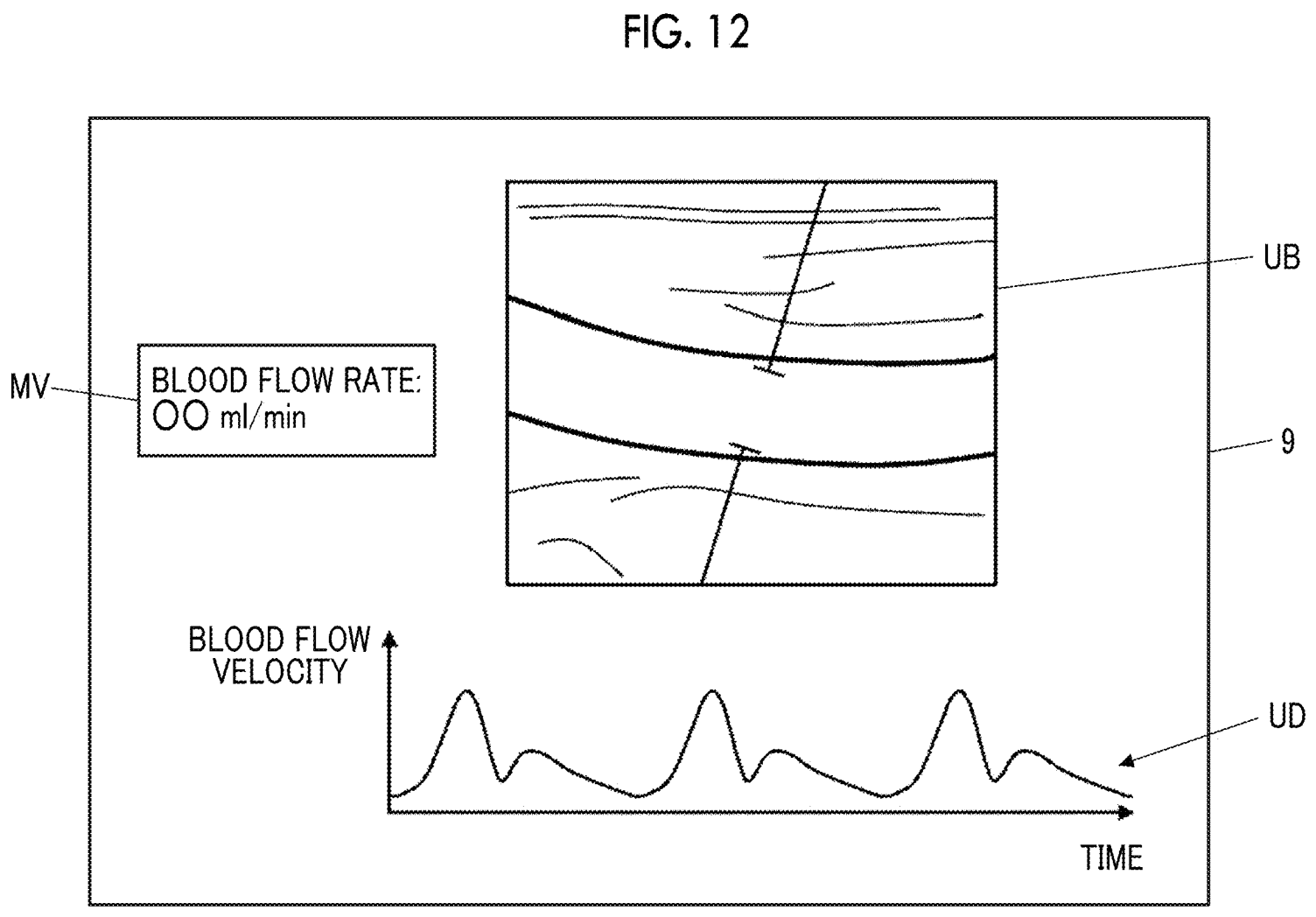

In Step S8, the blood flow rate measurement unit 15 measures the blood flow rate representing the volume of the blood flowing in the blood vessel per unit time on the basis of the cross-sectional area of the blood vessel that is calculated on the basis of the minimum diameter, the maximum diameter, or the average diameter of the blood vessel in Step S6, and the blood flow velocity calculated in Step S7, and causes the display device 9 to display a measurement value MV of the blood flow rate as illustrated in FIG. 12. In the example illustrated in FIG. 9, the measurement value MV of the blood flow rate is displayed together with the B-mode image UB and the Doppler waveform image UD on the display device 9.

In a case where the blood flow rate is measured in Step S8 in this manner, the operation of the ultrasound diagnostic apparatus 1 is ended.

Here, in a case where the blood flow rate is measured on the basis of the B-mode image of the frame selected by the user because the image is clear among the B-mode images of the series of frames, the condition that the blood vessel has the minimum diameter or the condition that has the maximum diameter is different each time the blood flow rate is measured, and thus there is a problem that it is difficult to perform an accurate comparison in a case where the measurement value of the blood flow rate measured in the past and the value of the blood flow rate that is newly measured are compared for the same subject.

In the ultrasound diagnostic apparatus 1 according to the first embodiment of the present invention, since the blood flow rate is measured in Step S8 on the basis of the cross-sectional area of the blood vessel calculated on the basis of the minimum diameter, the maximum diameter, or the average diameter of the blood vessel in Step S6, and the blood flow velocity calculated in Step S7, the blood flow rate is calculated according to a certain criterion. Therefore, for example, in a case where the measurement value of the blood flow rate measured in the past and the value of the measurement value that is newly measured are compared, it is possible to perform an accurate comparison according to a certain condition.

As described above, with the ultrasound diagnostic apparatus 1 according to the first embodiment of the present invention, since at least one of the B-mode image signal of the frame with the minimum diameter of the blood vessel or the B-mode image signal of the frame with the maximum diameter of the blood vessel in the time phase search period specified by the time phase search period specifying unit 16 is specified, at least one of the B-mode image signal of the frame with the minimum diameter of the blood vessel or the B-mode image signal of the frame with the maximum diameter of the blood vessel can be specified with a smaller amount of calculation than in a case where all the B-mode image signals generated together with the Doppler waveform image signals in a predetermined period are used. Therefore, the burden on the ultrasound diagnostic apparatus 1 can be reduced, and at least one of the B-mode image signal of the frame with the minimum diameter of the blood vessel or the B-mode image signal of the frame with the maximum diameter of the blood vessel can be easily specified in a short time.

With the ultrasound diagnostic apparatus 1, in a case where at least one of the B-mode image signal of the frame with the minimum diameter of the blood vessel or the B-mode image signal with the maximum diameter of the blood vessel is specified, the diameters of the blood vessels in the B-mode image signals in at least one of the first period FP or the second period SP may be compared with each other, and it is possible to reduce a possibility that the B-mode image signal in which the brightness value fluctuates due to the influence of noise or the like is erroneously specified. Therefore, at least one of the minimum diameter or the maximum diameter of the blood vessel can be accurately calculated by the blood vessel diameter calculation unit 13, and an accurate value can be measured for the blood flow rate calculated by the blood flow rate measurement unit 15.

The time phase search period specifying unit 16 specifies the second period SP as a period from the time point T2 at which the blood flow velocity has the maximum value V2 to the time point T3 after a predetermined time set to a time shorter than each heartbeat period HC, for example, 0.25 seconds or the like has elapsed from the time point T2, with respect to the first period FP from the time point T1 at which the blood flow velocity in the Doppler waveform image UD has the minimum value V1 to the time point T2 at which the blood flow velocity has the maximum value V2, but the method of specifying the second period SP is not limited thereto.

For example, the time phase search period specifying unit 16 can specify, as the second period SP, a period from the time point T2 at which the blood flow velocity has the maximum value V2 to the time point T3 after a predetermined time has elapsed from the time point T2 such that the sum of the first period FP and the second period SP has a time width that is a half of the heartbeat period HC.

For example, the time phase search period specifying unit 16 can specify, as the second period SP, a period from the time point T2 at which the blood flow velocity has the maximum value V2 to the time point T3 after a predetermined time has elapsed from the time point T2 such that the second period SP has a time width of 10% or more and 20% or less of the heartbeat period HC. In this case, it is preferable that the first period FP has a time width of 10% or more and 20% or less of the heartbeat period HC.

Further, for example, the time phase search period specifying unit 16 can specify, as the second period SP, a period from the time point T2 at which the blood flow velocity has the maximum value V2 to the time point T3 after a predetermined time has elapsed from the time point T2 such that the second period SP has the same time width as the first period FP.

The B-mode image signals and the Doppler waveform image signals are continuously generated for a predetermined period by the B-mode processing unit 6 and the Doppler processing unit 7, but instead of generating the B-mode image signals and the Doppler waveform image signals, a memory (not illustrated) in which the B-mode image signals generated for a predetermined period and the Doppler waveform image signals generated for the same predetermined period are saved in advance may be included in the ultrasound diagnostic apparatus 1. In this case, the time phase search period is specified by the time phase search period specifying unit 16 on the basis of the Doppler waveform image signal saved in the memory (not illustrated), and at least one of the B-mode image signal of the frame with the minimum blood vessel diameter or the B-mode image signal of the frame with the maximum blood vessel diameter is specified by the frame specifying unit 12 on the basis of the B-mode image signals of the plurality of frames in the time phase search period among the B-mode image signals of the plurality of frames saved in the memory (not illustrated).

Therefore, instead of generating the B-mode image signals and the Doppler waveform image signals, even in a case where the memory (not illustrated) in which the B-mode image signals generated for a predetermined period and the Doppler waveform image signals generated for the same predetermined period are saved in advance is included in the ultrasound diagnostic apparatus 1, similar to the case where the B-mode image signals and the Doppler waveform image signals are generated, in the ultrasound diagnostic apparatus 1, the burden in a case where at least one of the B-mode image signal of the frame with the minimum diameter of the blood vessel or the B-mode image signal of the frame with the maximum diameter of the blood vessel is specified can be reduced, and at least one of the B-mode image signal of the frame with the minimum diameter of the blood vessel or the B-mode image signal of the frame with the maximum diameter of the blood vessel can be easily specified in a short time. In the ultrasound diagnostic apparatus 1, it is possible to reduce a possibility that the B-mode image signal in which the brightness value fluctuates due to the influence of noise or the like is erroneously specified.

Figure 10:
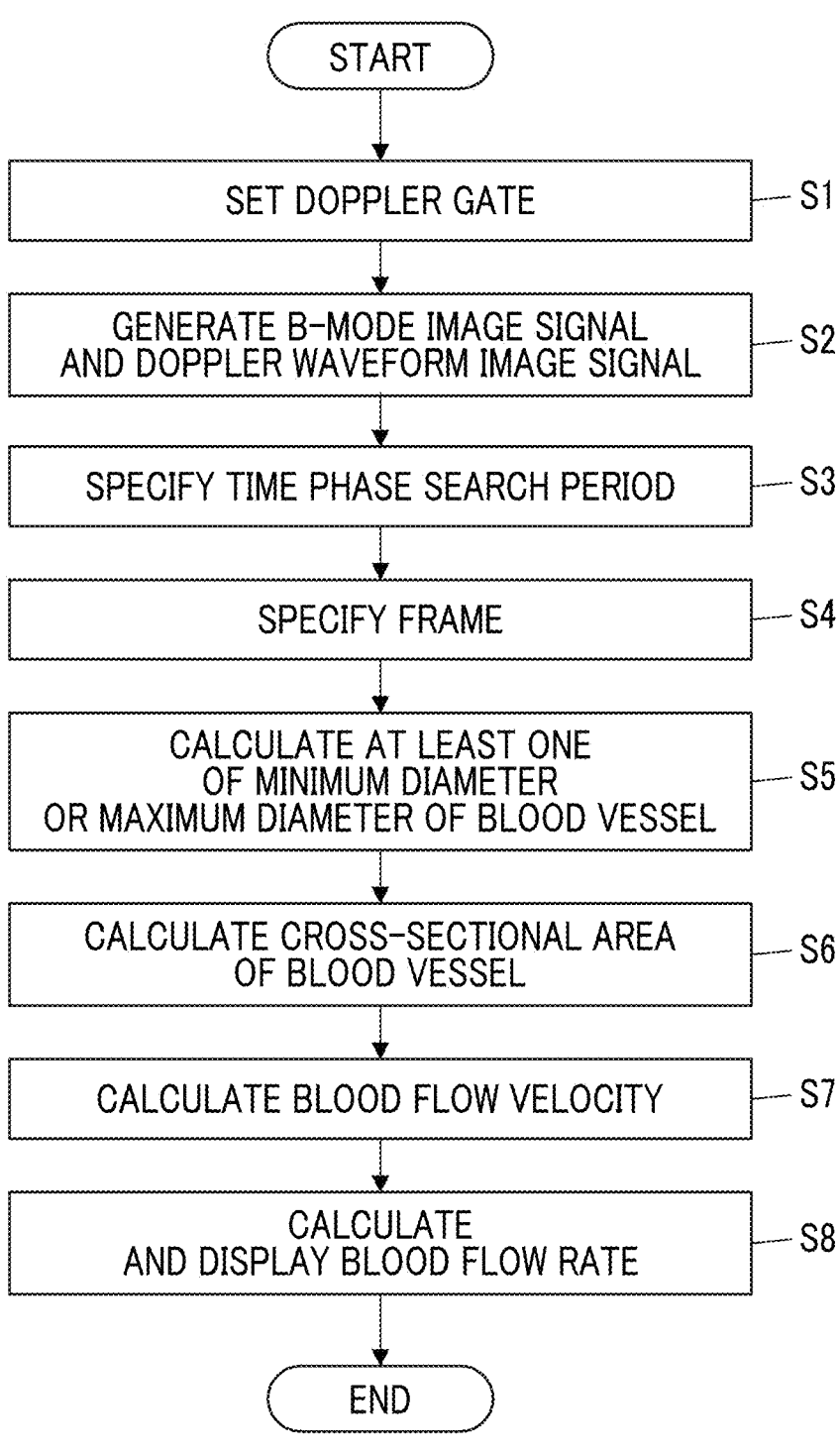
FIG. 10 is a flowchart illustrating an operation of the ultrasound diagnostic apparatus according to the first embodiment of the present invention.

In step S2 of the flowchart in FIG. 10, the B-mode image signals and the Doppler waveform image signals are generated for a predetermined period by the B-mode processing unit 6 and the Doppler processing unit 7, and then, in Step S3, the time phase search period is specified, but processing of specifying the time phase search period may be performed in real time on the basis of the Doppler waveform image signals sequentially generated in the predetermined period in Step S2 may be performed. In this case, the time phase search period specifying unit 16 performs processing of specifying the time phase search period on the basis of the generated Doppler waveform image signal each time the Doppler processing unit 7 generates the Doppler waveform image signal in a period less than the heartbeat period HC. In this case, since it is not necessary for the B-mode processing unit 6 and the Doppler processing unit 7 to acquire the B-mode image signals and the Doppler waveform image signals after the first period FP or after the second period SP, at least one of the B-mode image signal with the minimum diameter of the blood vessel or the B-mode image signal with the maximum diameter of the blood vessel is specified more quickly and easily.

The frame specifying unit 12 can specify RF data of a frame with the minimum diameter of the blood vessel and RF data of a frame with the maximum diameter of the blood vessel on the basis of the RF data generated by the reception circuit 4 instead of specifying the B-mode image signal of the frame with the minimum diameter of the blood vessel and the B-mode image signal of the frame with the maximum diameter of the blood vessel on the basis of the B-mode image signals generated by the B-mode processing unit 6. Even in this case, similar to the case where the B-mode image signal of the frame with the minimum diameter of the blood vessel and the B-mode image signal of the frame with the maximum diameter of the blood vessel are specified on the basis of the B-mode image signals by the frame specifying unit 12, the burden on the ultrasound diagnostic apparatus 1 can be reduced, and the RF data of the frame with the minimum diameter of the blood vessel and the RF data of the frame with the maximum diameter of the blood vessel can be easily and accurately specified.

Second Embodiment

In the first embodiment, both the B-mode image signal of the frame with the minimum diameter of the blood vessel and the B-mode image signal of the frame with the maximum diameter of the blood vessel can be specified by the frame specifying unit 12, and both the minimum diameter and the maximum diameter of the blood vessel in each heartbeat period HC can be calculated by the blood vessel diameter calculation unit 13. However, for example, an elastic index indicating the elasticity of the blood vessel can be calculated using the minimum diameter and the maximum diameter of the blood vessel calculated as described above.

Figure 13:
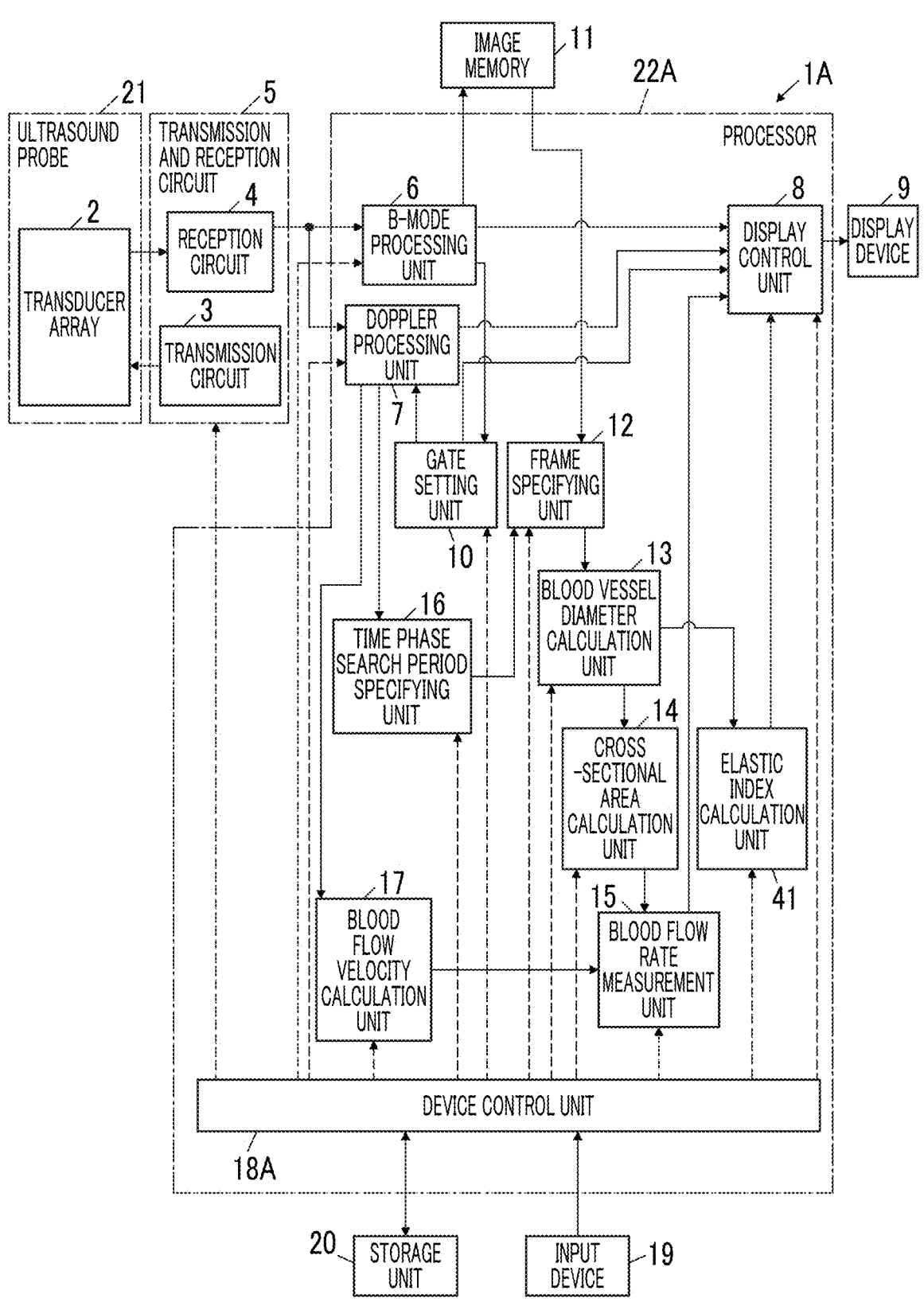
FIG. 13 is a block diagram illustrating an ultrasound diagnostic apparatus according to a second embodiment of the present invention.

As illustrated in FIG. 13, an ultrasound diagnostic apparatus 1A according to the second embodiment of the present invention is obtained by comprising a device control unit 18A instead of the device control unit 18 and adding an elastic index calculation unit 41 to the ultrasound diagnostic apparatus 1 of the first embodiment illustrated in FIG. 1.

In the ultrasound diagnostic apparatus 1A, the elastic index calculation unit 41 is connected to the blood vessel diameter calculation unit 13, and the display control unit 8 and the device control unit 18A are connected to the elastic index calculation unit 41. Further, the B-mode processing unit 6, the Doppler processing unit 7, the display control unit 8, the gate setting unit 10, the frame specifying unit 12, the blood vessel diameter calculation unit 13, the cross-sectional area calculation unit 14, the blood flow rate measurement unit 15, the time phase search period specifying unit 16, the blood flow velocity calculation unit 17, the device control unit 18A, and the elastic index calculation unit 41 constitute a processor 22A for the ultrasound diagnostic apparatus 1A.

The elastic index calculation unit 41 calculates an elastic index of the blood vessel on the basis of a difference between the maximum diameter and the minimum diameter of the blood vessel calculated by the blood vessel diameter calculation unit 13. The elastic index of the blood vessel is an index indicating the elasticity of the blood vessel. It can be determined that the larger the difference between the maximum diameter and the minimum diameter of the blood vessel, the larger the change in the diameter of the blood vessel and the lower the modulus of elasticity of the blood vessel, and it can be determined that the smaller the difference between the maximum diameter and the minimum diameter of the blood vessel, the smaller the change in the diameter of the blood vessel and the higher the modulus of elasticity of the blood vessel. Therefore, the elastic index calculation unit 41 can calculate the difference between the maximum diameter and the minimum diameter of the blood vessel as the elastic index of the blood vessel, for example. Further, the elastic index calculation unit 41 can also calculate a normalized value as the elastic index by dividing the difference between the maximum diameter and the minimum diameter of the blood vessel by the minimum diameter of the blood vessel.

By measuring a blood pressure P1 of the subject at the time point at which the diameter of the blood vessel is the minimum and a blood pressure P2 of the subject at the time point at which the diameter of the blood vessel is the maximum using a blood pressure manometer (not illustrated), the elastic index calculation unit 41 can calculate a stiffness parameter $B=\{Log(P2/P1)\}/\{(D2/D1)-1\}$ disclosed in JP5384919B as the elastic index using the blood pressures P1 and P2, the minimum value D1 of the diameter of the blood vessel in the heartbeat period HC, and the maximum value D2 of the diameter of the blood vessel in the heartbeat period HC.

As described above, with the ultrasound diagnostic apparatus 1A according to the second embodiment of the present invention, similar to the ultrasound diagnostic apparatus 1 according to the first embodiment, in a case where the B-mode image signal of the frame with the minimum diameter of the blood vessel and the B-mode image signal with the maximum diameter of the blood vessel are specified, the burden on the ultrasound diagnostic apparatus 1A can be reduced, the B-mode image signal of the frame with the minimum diameter of the blood vessel and the B-mode image signal with the maximum diameter of the blood vessel can be easily specified in a short time, and further a possibility that the B-mode image signal in which the brightness value fluctuates due to the influence of noise or the like is erroneously specified can be reduced. Therefore, it is possible to also easily and accurately calculate the elastic index in a short time.

Third Embodiment

The ultrasound diagnostic apparatus 1 of the first embodiment has the configuration in which the display device 9, the input device 19, and the ultrasound probe 21 are directly connected to the processor 22, but, for example, the display device 9, the input device 19, the ultrasound probe 21, and the processor 22 can be indirectly connected to each other via the network.

Figure 14:
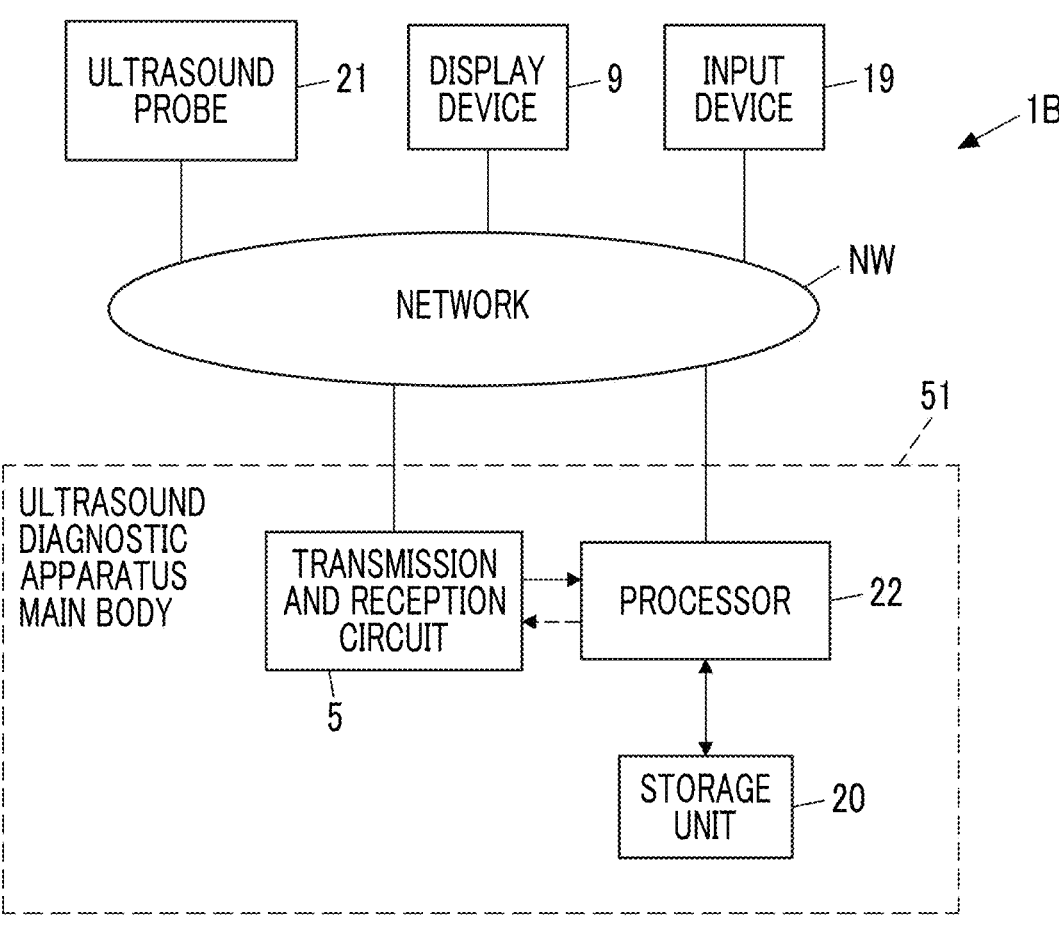
FIG. 14 is a block diagram illustrating an ultrasound diagnostic apparatus according to a third embodiment of the present invention.

As illustrated in FIG. 14, in an ultrasound diagnostic apparatus 1B in a third embodiment, the display device 9, the input device 19, and the ultrasound probe 21 are connected to an ultrasound diagnostic apparatus main body 51 via a network NW. The ultrasound diagnostic apparatus main body 51 is obtained by excluding the display device 9, the input device 19, and the ultrasound probe 21 in the ultrasound diagnostic apparatus 1 of the first embodiment illustrated in FIG. 1, and is constituted by the transmission and reception circuit 5, the storage unit 20, and the processor 22.

Even in a case where the ultrasound diagnostic apparatus 1B has such a configuration, similar to the ultrasound diagnostic apparatus 1 of the first embodiment, at least one of the B-mode image signal of the frame with the minimum diameter of the blood vessel or the B-mode image signal of the frame with the maximum diameter of the blood vessel in the time phase search period specified by the time phase search period specifying unit 16 is specified, and therefore, at least one of the B-mode image signal of the frame with the minimum diameter of the blood vessel or the B-mode image signal of the frame with the maximum diameter of the blood vessel can be specified with a smaller amount of calculation than in a case where all the B-mode image signals generated together with the Doppler waveform image signals in a predetermined period are used. Therefore, the burden on the ultrasound diagnostic apparatus 1 can be reduced, and at least one of the B-mode image signal of the frame with the minimum diameter of the blood vessel or the B-mode image signal of the frame with the maximum diameter of the blood vessel can be easily specified in a short time.

Further, with the ultrasound diagnostic apparatus 1B, similar to the ultrasound diagnostic apparatus 1 of the first embodiment, in a case where at least one of the B-mode image signal of the frame with the minimum diameter of the blood vessel or the B-mode image signal with the maximum diameter of the blood vessel is specified, the diameters of the blood vessels in the B-mode image signals in at least one of the first period FP or the second period SP may be compared with each other, and it is possible to reduce a possibility that the B-mode image signal in which the brightness value fluctuates due to the influence of noise or the like is erroneously specified.

Further, since the display device 9, the input device 19, and the ultrasound probe 21 are connected to the ultrasound diagnostic apparatus main body 51 via the network NW, the ultrasound diagnostic apparatus main body 51 can be used as a so-called remote server. Thereby, for example, since the user can perform a diagnosis of the subject by preparing the display device 9, the input device 19, and the ultrasound probe 21 at the user's hand, it is possible to improve the convenience in a case of the ultrasound diagnosis.

Further, in a case where a portable thin computer, for example, a so-called tablet, is used as the display device 9 and the input device 19, it is possible for the user to more easily perform the ultrasound diagnosis of the subject, and it is possible to further improve the convenience in a case of the ultrasound diagnosis.

The display device 9, the input device 19, and the ultrasound probe 21 are connected to the ultrasound diagnostic apparatus main body 51 via the network NW, but in this case, the display device 9, the input device 19, and the ultrasound probe 21 may be connected to the network NW in a wired manner or in a wireless manner.

Further, it is described that the form of the third embodiment is applied to the first embodiment, but the form of the third embodiment can be similarly applied to the second embodiment.

EXPLANATION OF REFERENCES 1, 1A, 1B: ultrasound diagnostic apparatus
2: transducer array
3: transmission circuit
4: reception circuit
5: transmission and reception circuit
6: B-mode processing unit
7: Doppler processing unit
8: display control unit
9: display device
10: gate setting unit
11: image memory
12: frame specifying unit
13: blood vessel diameter calculation unit
14: cross-sectional area calculation unit
15: blood flow rate measurement unit
16: time phase search period specifying unit
17: blood flow velocity calculation unit
18, 18A: device control unit
19: input device
20: storage unit
21: ultrasound probe
22, 22A: processor
23: amplification unit
24: AD conversion unit
25: beam former
26: signal processing unit
27: DSC
28: image processing unit
29: quadrature detection unit 30: high-pass filter
31: fast Fourier transformer
32: Doppler waveform image generation unit
33: data memory
41: elastic index calculation unit
51: ultrasound diagnostic apparatus main body
52: transmission and reception circuit
BR: blood vessel region
D1, V1: minimum value
D2, V2: maximum value
DG: Doppler gate
E: envelope curve
FP: first period
HC: heartbeat period
L: distance
MV: measurement value
SL: straight line
SP: second period
T1, T2, T3, T4: time point
UB: B-mode image
UD: Doppler waveform image
W1: anterior vascular wall
W2: posterior vascular wall
WD: Doppler waveform

What is claimed is:

1. An ultrasound diagnostic apparatus in which B-mode data and Doppler data of a region including a blood vessel of a subject are continuously acquired for a predetermined period, the ultrasound diagnostic apparatus comprising:
an ultrasound probe;
a transmission and reception circuit configured to transmit an ultrasound beam to an inside of the subject via the ultrasound probe, and receive an ultrasound echo from the inside of the subject to generate reception data; and
a processor configured to
generate the B-mode data on the basis of the reception data generated by the transmission and reception circuit,
specify at least one of a first period and a second period within each heartbeat period as a time phase search period, where each heartbeat period is composed of the first period, the second period, and a third period, the first period includes a time point at which the Doppler data has a minimum value, the second period includes a time point at which the Doppler data has a maximum value, the third period runs from an end of the second period to an end of each heartbeat period, and the first period, the second period, and the third period within any heartbeat period are different from each other,
calculate a diameter of the blood vessel included in the B-mode data of each of a plurality of frames only in the specified time phase search period within each heartbeat period, and
specify at least one of the B-mode data of a frame with a maximum diameter of the blood vessel or the B-mode data of a frame with a minimum diameter of the blood vessel within each heartbeat period based on the diameters of the blood vessel calculated from the B-mode data of the plurality of frames in the specified time phase search period.

2. The ultrasound diagnostic apparatus according to claim 1,
wherein the first period starts from the time point at which the Doppler data has the minimum value and ends with the time point at which the Doppler data has the maximum value in each heartbeat period.

3. The ultrasound diagnostic apparatus according to claim 1, wherein the second period starts from a first time point at which the Doppler data has the maximum value and ends with a second time point which is after the first time point, where a time span between the first time point and the second time point is set to be shorter than each heartbeat period.

4. The ultrasound diagnostic apparatus according to claim 1, wherein each of the first period and the second period has a time width of 10% or more and 20% or less of each heartbeat period.

5. The ultrasound diagnostic apparatus according to claim 1, wherein the processor is further configured to calculate at least one of the maximum diameter or the minimum diameter of the blood vessel on the basis of at least one of the B-mode data of the frame with the maximum diameter of the blood vessel or the B-mode data of the frame with the minimum diameter of the blood vessel.

6. The ultrasound diagnostic apparatus according to claim 5, wherein the processor is further configured to calculate a cross-sectional area of the blood vessel using at least one of the maximum diameter or the minimum diameter of the blood vessel, acquire the Doppler data in each heartbeat period, calculate a blood flow velocity on the basis of the Doppler data acquired, and measure a blood flow rate on the basis of the cross-sectional area and the blood flow velocity.

7. The ultrasound diagnostic apparatus according to claim 5, wherein the first period starts from the time point at which the Doppler data has the minimum value and ends with the time point at which the Doppler data has the maximum value in each heartbeat period.

8. The ultrasound diagnostic apparatus according to claim 5, wherein the second period starts from a first time point at which the Doppler data has the maximum value and ends with a second time point which is after the first time point, where a time span between the first time point and the second time point is set to be shorter than each heartbeat period.

9. The ultrasound diagnostic apparatus according to claim 5, wherein each of the first period and the second period has a time width of 10% or more and 20% or less of each heartbeat period.

10. The ultrasound diagnostic apparatus according to claim 6, wherein the processor is further configured to specify the B-mode data of the frame with the minimum diameter of the blood vessel on the basis of the B-mode data of the plurality of frames in the first period, calculate the minimum diameter of the blood vessel on the basis of the B-mode data of the frame with the minimum diameter of the blood vessel, and calculate the cross-sectional area of the blood vessel using the minimum diameter of the blood vessel.

11. The ultrasound diagnostic apparatus according to claim 6, wherein the processor is further configured to specify the B-mode data of the frame with the maximum diameter of the blood vessel on the basis of the B-mode data of the plurality of frames in the second period, calculate the maximum diameter of the blood vessel on the basis of the B-mode data of the frame with the maximum diameter of the blood vessel specified, and calculate the cross-sectional area of the blood vessel using the maximum diameter of the blood vessel calculated.

12. The ultrasound diagnostic apparatus according to claim 6, wherein each of the first period and the second period has a time width of 10% or more and 20% or less of each heartbeat period.

13. The ultrasound diagnostic apparatus according to claim 6, wherein the processor is further configured to specify the B-mode data of the frame with the minimum diameter of the blood vessel on the basis of the B-mode data of the plurality of frames in the first period, and specifies the B-mode data of the frame with the maximum diameter of the blood vessel on the basis of the B-mode data of the plurality of frames in the second period, calculate the minimum diameter of the blood vessel on the basis of the B-mode data of the frame with the minimum diameter of the blood vessel, calculate the maximum diameter of the blood vessel on the basis of the B-mode data of the frame with the maximum diameter of the blood vessel, and calculate the cross-sectional area of the blood vessel using an average diameter of the blood vessel in each heartbeat period calculated from the minimum diameter of the blood vessel and the maximum diameter of the blood vessel calculated.

14. The ultrasound diagnostic apparatus according to claim 13, wherein the processor is further configured to calculate an elastic index of the blood vessel on the basis of a difference between the maximum diameter of the blood vessel and the minimum diameter of the blood vessel.

15. A control method of an ultrasound diagnostic apparatus in which B-mode data and Doppler data of a region including a blood vessel of a subject are continuously acquired for a predetermined period, the control method comprising:

transmitting an ultrasound beam to an inside of the subject via an ultrasound probe and receiving an ultrasound echo from the inside of the subject to generate reception data;

generating the B-mode data on the basis of the reception data;

specifying at least one of a first period and a second period as a time phase search period within each heartbeat period, where each heartbeat period is composed of the first period, the second period, and a third period, the first period includes a time point at which the Doppler data has a minimum value, the second period includes a time point at which the Doppler data has a maximum value, the third period runs from an end of the second period to an end of each heartbeat period, and the first period, the second period, and the third period within any heartbeat period are different from each other;

calculating a diameter of the blood vessel included in the B-mode data of each of a plurality of frames only in the specified time phase search period within each heartbeat period; and specifying at least one of the B-mode data of a frame with a maximum diameter of the blood vessel or the B-mode data of a frame with a minimum diameter of the blood vessel within each heartbeat period based on the diameters of the blood vessel calculated from the B-mode data of the plurality of frames in the specified time phase search period.

16. An ultrasound diagnostic apparatus in which B-mode data and Doppler data of a region including a blood vessel of a subject are continuously acquired for a predetermined period, the ultrasound diagnostic apparatus comprising:

an ultrasound probe;

a transmission and reception circuit configured to transmit an ultrasound beam to an inside of the subject via the ultrasound probe, and receive an ultrasound echo from the inside of the subject to generate reception data; and a processor configured to generate the B-mode data on the basis of the reception data generated by the transmission and reception circuit, specify at least one of a first period and a second period within each heartbeat period as a time phase search period, where a first period starts from a first time point at which the Doppler data has a minimum value and ends with a second time point at which the Doppler data has a maximum value within each heartbeat period, a second period starts from the second time point and ends with a third time point within each heartbeat period, the third period runs from an end of the second period to an end of each heart beat period, and the first period and the second period within any heartbeat period are different from each other, calculate a diameter of the blood vessel included in the B-mode data of each of a plurality of frames only in the specified time phase search period within each heartbeat period, and specify at least one of the B-mode data of a frame with a maximum diameter of the blood vessel or the B-mode data of a frame with a minimum diameter of the blood vessel within each heartbeat period based on the diameters of the blood vessel calculated from the B-mode data of the plurality of frames in the specified time phase search period.

\* \* \* \* \*